United States Patent [19]

Lavielle et al.

[11] Patent Number: 4,567,169

[45] Date of Patent: Jan. 28, 1986

[54] NITROSOUREA SUBSTITUTED PHOSPHONATES AND PHARMACEUTICAL USE

[75] Inventors: Gilbert Lavielle, Orleans; Claude Cudennec, La Celle Saint Cloud, both of France

[73] Assignee: ADIR, S.A.R.L., Neuilly-sur-Seine, France

[21] Appl. No.: 547,881

[22] Filed: Nov. 2, 1983

[30] Foreign Application Priority Data

Nov. 17, 1982 [FR] France .................................. 82 19199

[51] Int. Cl.⁴ .................... A61K 31/66; A61K 31/675; C07F 9/40; C07F 9/58
[52] U.S. Cl. ..................................... 514/089; 260/923; 546/22; 548/112; 549/6; 514/91; 514/95; 514/114
[58] Field of Search ................ 260/923, 938; 514/114, 514/89, 91, 95; 546/22; 548/112; 549/6

[56] References Cited

U.S. PATENT DOCUMENTS 3,920,733 11/1975 Birum .................................. 260/938

OTHER PUBLICATIONS

Appendix I, "Clinical Predictivity of Transplantable Tumor Systems in the Selection of New Drugs for Solid Tumors: Rationale for a Three-Stage Strategy"; Cancer Treatment Reports, vol. 67, No. 9, Sep. 1983, pp. 753-765.

Appendix II, Physicians' Desk Reference, 38th Edition, 1984, p. 735.

*Primary Examiner*—Anton H. Sutto
*Attorney, Agent, or Firm*—Gordon W. Hueschen

[57] ABSTRACT

New nitrosourea compounds that can be used as medicaments and correspond to the general formula I

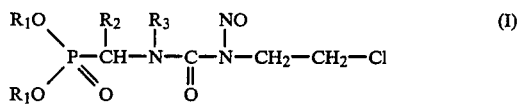

in which $R_1$ is hydrogen, $C_1$-$C_6$ alkyl or phenyl, $R_2$ is hydrogen, $C_1$-$C_6$ alkyl, thienyl, or phenyl which may carry substituents, $R_3$ is hydrogen, $C_1$-$C_6$ alkyl, or benzyl which may carry substituents, or $R_2$ and $R_3$ together represent —$(CH_2)_m$—, m being 3 or 4.

Pharmaceutical compositions; therapeutic administration especially for the treatment of tumours.

7 Claims, No Drawings

NITROSOUREA SUBSTITUTED PHOSPHONATES AND PHARMACEUTICAL USE

The present invention relates to new nitrosourea compounds, process for the preparation thereof and pharmaceutical compositions containing them.

It relates especially to nitrosourea compounds of the general formula I $$\begin{array}{c} R_1O \\ \phantom{R_1O}\diagdown \\ \phantom{R_1O}\phantom{\diagdown}P-CH-N-C-N-CH_2-CH_2-Cl \\ \phantom{R_1O}\diagup \phantom{\diagdown}\| \phantom{CH}|\phantom{N}\|\| \\ R_1O \phantom{\diagup}O \phantom{CH-N}O \end{array} \quad (I)$$

with $R_2$, $R_3$, NO on the nitrogen/carbon positions.

in which
$R_1$ represents a hydrogen atom, a straight-chain or branched alkyl radical containing from 1 to 6 carbon atoms; or a phenyl radical which may carry as substituent a halogen atom or an alkyl or alkoxy radical containing from 1 to 5 carbon atoms;
$R_2$ represents a hydrogen atom, a straight-chain or branched alkyl radical containing from 1 to 6 carbon atoms and which may carry a carboxy or alkoxycarbonyl radical including from 2 to 6 carbon atoms; a thienyl, phenyl or benzyl radical which may carry as substituent a halogen atom or an alkyl or alkoxy radical each containing from 1 to 5 carbon atoms;
$R_3$ represents a hydrogen atom, a straight-chain or branched alkyl radical having from 1 to 6 carbon atoms, or a benzyl radical which may carry as substituent a halogen atom or an alkyl or alkoxy radical each having from 1 to 5 carbon atoms; or, alternatively,
$R_2$ and $R_3$ together represent a group $-(CH_2)_m-$ in which m has the value 3 or 4, in racemic form or in the form of optical isomers.

The subject of the present invention is also a process for the preparation of compounds of the general formula I, characterised in that an α-aminophosphonate compound of the general formula II $$\begin{array}{c} R_1O \\ \phantom{R_1O}\diagdown \\ \phantom{R_1O}\phantom{\diagdown}P-CH-NH \\ \phantom{R_1O}\diagup \phantom{\diagdown}\| \phantom{CH}| \\ R_1O \phantom{\diagup}O \phantom{CH}R_3 \end{array} \quad (II)$$

with $R_2$ substituent.

in which $R_1$, $R_2$ and $R_3$ have the meanings defined above for the formula I, is condensed with an excess of β-chloroethyl isocyanate of the formula III $$Cl-CH_2-CH_2-N=C=O \quad (III)$$

to give new compounds of the general formula IV $$\begin{array}{c} R_1O \\ \phantom{R_1O}\diagdown \\ \phantom{R_1O}\phantom{\diagdown}P-CH-N-C-NH-CH_2-CH_2-Cl \\ \phantom{R_1O}\diagup \phantom{\diagdown}\| \phantom{CH}|\phantom{N}|\| \\ R_1O \phantom{\diagup}O \phantom{CH}R_3 O \end{array} \quad (IV)$$

with $R_2$ substituent.

in which $R_1$, $R_2$ and $R_3$ have the meanings defined above, and the nitroso group is introduced into the compounds of the formula IV to give compounds of the formula I.

The condensation is preferably carried out in water or in a solvent selected from the chlorinated solvents, such as, for example, chloroform. It is advantageous to operate at a temperature between 0° and 10° C., optionally in the presence of a mineral or organic base.

The introduction of the nitroso group into the new compounds (IV) to form nitrosoureas of the general formula I is carried out, for example, by the action of sodium nitrite in formic acid cooled to 5° C. or, alternatively, by nitrosyl chloride in a solvent, such as pyridine, for several hours at a temperature of 0° C., according to the methods described by J. L. MONTERO et al. in Eur. J. Med. Chem. 1981, 16, 539.

The starting materials of the general formula II are α-aminophosphonic acids or α-aminophosphonates which are already known in the literature; the main processes for the synthesis of these compounds have been described by:

K. D. BERLIN, R. T. CLAUNCH and E. T. GAUDY in J. Org. Chem. 1968, 33, 3090

J. KOWALIK and P. MASTALERZ in Synthesis 1981, 57

J. OLEKSYSZYN and R. TYKA in Tetrahedron Letters, 1977, 22, 2823, and

A. DEHNEL and G. LAVIELLE in Bull. Soc. Chim. Fr. 1978, 95.

All the new compounds forming part of this invention can be purified by physical methods such as crystallisation or chromatography.

The present invention also relates to the optical isomers of the compounds corresponding to the general formula I. These isomers may be prepared from optically active forms of the general formula II by resolution of the racemic compounds.

There may be mentioned as resolving agent, for example, (+) and (−) dibenzoyltartaric acids.

The compounds of the general formula I have interesting pharmacological and therapeutic properties. These compounds have an anti-bacterial activity. In addition, the pharmacological properties of these compounds make them more interesting for the potential treatment of tumors than the nitrosoureas which are used as references and which have long been recognised as having oncolytic and oncostatic activities.

The compounds according to the invention are tested by their capacity to increase the life-span of mice bearing tumorous cells inoculated by intraperitoneal or intramuscular route in accordance with the protocols edicted by the National Cancer Institute (U.S.A.) and published by R. I. GERAN et al. in Cancer Chemotherapy Reports 1972, part III, Vol. 3 (2), 1-87.

It was found that when administered by intraperitoneal route the compounds according to the invention are capable of prolonging the life-span of tumour-bearing mice at a dose of 1 mg/kg and above and of inducing long-term survivors at a dose of 5 mg/kg as is the case for the compound of example 4. Given per os, these compounds increase the life-span of tumor-bearing animals. The rate of effectiveness of the active doses per os over the active dose by intraperitoneal route is greater for the compounds according to the invention than for the reference products (F. SPREAFICO et al. in Nitrosoureas: current status and new developments, A. W. PRESTAYKO et al. editors, 1981, Academic Press (New York); Experimental Evaluation of Antitumor Drugs in the USA and USSR and clinical correlations; National Cancer Institute Monograph No. 55; National Institutes of Health USA 1980).

The compounds according to the invention can slow down the development of tumor cells which have been inoculated intrathecally, thus proving their capacity to cross the blood-brain barrier. In the same way, these compounds are capable of inhibiting the growth of carcinomas grafted into the muscle or under the skin of a mouse even when treatment only begins several days after the grafting.

The antimetastatic capacity of the compounds of the present invention is measured by the reduction, compared with untreated animals, in the number and weight of pulmonary metastases developed after intramuscular inoculation of carcinoma cells. The compounds according to the invention reduce or prevent development of the metastases, for example compound No. 4 prevents the formation of metastases when it is administered at a dose of 10 mg/kg as a curative treatment for 9 days.

The haemotopoietic toxicity is assessed, in animals treated with one or several administrations of the compounds according to the invention, by the count of the peripheral blood cells and of the bone marrow, and the stem cells contained in the bone marrow (J. E. TILL and E. A. McCULLOCH, 1961, Radiation Res., 14, 213). The nadir of cellular concentrations thus calculated is noted 3 days after the start of treatment. The extent of this decrease is measured after treatment with one dose of N-N'-bis(2-chloroethyl)-N-nitrosourea ("BCNU")-compound used as a reference (W. C. TANG and G. EISENBRAND, Arch. Pharm. 1981, 314, 910)—known to be the most effective against cancerous tumours, and with doses of compounds according to the invention having the same beneficial therapeutic effect. The recovery of the normal blood cell composition occurs on the tenth day after the start of treatment by the compounds of the invention, i.e. more rapidly than after administration of 25 mg/kg of BCNU. Moreover, the new compounds display less toxic side effects on the bone marrow renewing cells.

The hepatic toxicity is assessed according to Wroblewski's method by measuring the pyruvic glutamic transaminase activity contained in the serum from Long Evans rats treated with an intraperitoneal injection of 25 mg/kg of BCNU or with equipotential doses of the compounds according to the invention. Unlike BCNU, the products according to the invention do not show a notable hepatic toxicity. For example, treatment with 25 mg/kg of compound No. 4 does not lead to an increase in the enzyme level outside the range usually found in untreated rats.

The compounds according to the invention are used in oral or parental treatment of animals for the alleviation or mitigation of tumors which are responsive to treatment therewith.

The present invention also relates to pharmaceutical compositions useful for such antineoplastic therapy containing as active ingredient a derivative of the general formula I in admixture or in association with a pharmaceutically suitable excipient.

The pharmaceutical compositions so obtained are advantageously presented in various forms such as, for example, tablets, dragées, soft gelatine capsules, glossettes or galenic preparations suitable for sublingual administration, suppositories or solutions for injecting or drinking.

The following examples, which are not limiting, illustrate the invention. Unless otherwise stated, the melting points were determined on a Kofler heating block.

EXAMPLE 1

1-[N-(2-chloroethyl)-N-nitrosoureido]-ethylphosphonic acid (a) Preparation of 1-[N-(2-chloroethyl)ureido]ethylphosphonic acid 32 ml of a 1N sodium hydroxide solution is added to a solution of 2 g of α-aminoethylphosphonic acid in 20 ml of water, the reaction medium being cooled to 0° C. An equivalent (1.4 ml) of chloroethyl isocyanate is then added, still at the same temperature. After the addition, stirring is carried out for approximately 30 minutes at ambient temperature. A further equivalent of β-chloroethyl isocyanate (1.4 ml) is added and stirring is maintained for a further 2 hours. When stirring is completed, the precipitate formed during the reaction is separated by filtration and the aqueous solution is poured onto 30 ml of resin AG 50 W-X4, recovered and evaporated to dryness. The residue is partially dissolved in a few milliliters of boiling ethyl alcohol, then filtered hot to give 0.3 g of starting material which has not reacted. After evaporation of the ethanol, the residue obtained is recrystallised in water. Yield: 54%; m.p.=180° C.

Analysis: Calculated: C, 26.03; H, 5.21; N, 12.15; Cl, 15.40. Found: C, 26.32; H, 5.22; N, 12.20; Cl, 15.14.

(b) Preparation of 1-[N-(2-chloroethyl)-N-nitrosoureido]-ethylphosphonic acid

A solution containing 1 g of the 1-[N-(2-chloroethyl)ureido]ethylphosphonic acid obtained above in 20 ml of formic acid is cooled to 0° C. 1 g of sodium nitrite is then added in small portions and after stirring has been carried out for 30 minutes the solution is diluted with 100 ml of water. The solution is passed over 40 ml of resin AG 50 W-X4, then evaporated in vacuo without exceeding a temperature of 30° C. The yellow oil obtained (1 g) is slightly unstable and is not further purified. It is identified as 1-[N-(2-chloroethyl)-N-nitrosoureido]ethylphosphonic acid by customary physical methods (NMR; IR: see table).

EXAMPLE 2

α-[N-(2-chloroethyl)-N-nitrosoureido]-benzylphosphonic acid

α-[N-(2-chloroethyl)ureido]benzylphosphonic acid is prepared by the action of β-chloroethyl isocyanate and α-aminobenzylphosphonic acid according to the method described in Example 1a. Yield: 75%; m.p.=195° C.

Analysis: Calculated: C, 49.33; H, 5.87; N, 10.28; Cl, 8.69. Found: C, 49.03; H, 5.70; N, 10.26; Cl, 8.22.

The α-[N-(2-chloroethyl)-N-nitrosoureido]benzylphosphonic acid is obtained according to Example 1b by the action of sodium nitrite on the above acid urea. Yield: 56%, slightly unstable yellow oil. Physical data: see table.

EXAMPLE 3

α-[N-(2-chloroethyl)-N-nitrosoureido]-benzylphosphonic acid diethyl ester (a) Preparation of α-[N-(2-chloroethyl)ureido]benzylphosphonic acid diethyl ester A solution of 0.05 mol of α-aminobenzylphosphonic acid diethyl ester in 30 ml of chloroform is cooled to 0° C. in an ice-bath and then a large excess (0.06 mol) of β-chloroethyl isocyanate is added. The temperature of the reaction is then maintained at 10° C. while continuing stirring until the reaction is complete. (Examination by thin layer chromatography is used to ascertain that the starting aminophosphonate has disappeared completely. After evaporation of the solvent under reduced pressure, the crystalline residue is taken up in ether and filtered, yielding 14.8 g of crystals. Yield: 85%; m.p.=82° C.

(b) Preparation of α-[N-(2-chloroethyl)-N-nitrosoureido]-benzylphosphonic acid diethyl ester The urea obtained above (0.02 mol) is dissolved in 60 ml of formic acid and cooled to 5° C. Over a period of 1 hour, an excess of sodium nitrite (0.08 mol) is then added in small portions.

After evaporation of the formic acid in vacuo at a temperature of less than 35° C., the residue is taken up in 200 ml of dichloromethane, then washed 3 times with 100 ml of distilled water. The organic phase is then dried over sodium sulphate, filtered and evaporated under reduced pressure, leaving 5.5 g of an oil which is then chromatographed according to the technique described by W. C. STILL in J. Org. Chem. 1978, 43, 2923 using a mixture of $CH_2Cl_2$/MeOH (99/1) as eluant. The oil so obtained (4.7 g) crystallises in isopropyl ether, yielding crystals melting at 95° C. Yield: 62%.

EXAMPLES 4 TO 16

The following compounds were prepared according to the process described in Example 3:

(4) 1-[N-(2-chloroethyl)-N-nitrosoureido]ethylphosphonic acid diethyl ester: Yield: 52%; m.p.=85° C.

(5) α-[N-(2-chloroethyl)-N-nitrosoureido]-(4-chlorobenzyl)-phosphonic acid diethyl ester: Yield: 68%; m.p.=95° C.

(6) α-[N-(2-chloroethyl)-N-nitrosoureido]-(4-fluorobenzyl)phosphonic acid diethyl ester: Yield: 74%; m.p.=95° C.

(7) 1-[N-(2-chloroethyl)-N-nitrosoureido]-2-methylpropylphosphonic acid diethyl ester: Yield: 68%.

(8) 1-[N-(2-chloroethyl)-N-nitrosoureido]butylphosphonic acid diethyl ester: Yield: 58%.

(9) 1-[N-(2-chloroethyl)-N-nitrosoureido]-2-(4-methoxyphenyl)ethylphosphonic acid diethyl ester: Yield: 52%; m.p.=98° C.

(10) 1-[N-(2-chloroethyl)-N-nitrosoureido]-2-phenylethylphosphonic acid diethyl ester: Yield: 46%; m.p.=68° C.

(11) 2-{1-[N-(2-chloroethyl)-N-nitrosoureido]pyrrolidinyl}-phosphonic acid diethyl ester: Yield: 48%.

(12) 1-[N-(2-chloroethyl)-N-nitrosoureido]-2-(2-chlorophenyl)ethylphosphonic acid diethyl ester: Yield: 62%; m.p.=108° C.

(13) [N-(2-chloroethyl)-N-nitrosoureido]-(2-thienyl)methylphosphonic acid diethyl ester: Yield: 35%; m.p.=70° C.

(14) α-[N-(2-chloroethyl)-N-nitrosoureido]benzylphosphonic acid diethyl ester, laevorotatory isomer of Example 3: Yield: 35%; $\alpha_D^{22} = -34.4°$ (c=2; $CHCl_3$).

(15) α-[N-(2-chloroethyl)-N-nitrosoureido]benzylphosphonic acid diethyl ester, dextrorotatory isomer of Example 3: Yield: 43%; $\alpha_D^{22} = +36°$ (c=2; $CHCl_3$).

(16) [N-(2-chloroethyl)-N-nitroso-N'-benzylureido]methylphosphonic acid diethyl ester.

The starting [N-(2-chloroethyl)-N'-benzylureido]methylphosphonic acid diethyl ester is prepared according to the process described in Example 1.

The introduction of the nitroso group into the above urea is carried out using nitrosyl chloride according to the following method: 0.02 mol of the urea obtained according to the process described in Example 1 is dissolved in dichloromethane and, after cooling to −10° C., first 7 ml of nitrosyl chloride and then 15 ml of pyridine are added. After stirring for 2 hours at 0° C., the reaction mixture is poured into 250 ml of ice-water and then extracted using 3 portions of 100 ml of dichloromethane. The combined organic phases are first washed with 2 portions of 50 ml of 5% hydrochloric acid and finally with water. After drying over sodium sulphate, the organic phase is evaporated under reduced pressure and 7 g of an oil are obtained which is chromatographed using a mixture of chloroform/ethyl acetate (95/5) as eluant. Yield: 70%.

(17) 1-[N-(2-chloroethyl)-N-nitrosoureido]ethylphosphonic acid diphenyl ester: Yield: 80%; m.p.=84° C.

(18) 1-[N-(2-chloroethyl)-N-nitrosoureido]ethylphosphonic acid di(2-methoxyphenyl)ester: Yield: 85%; m.p.=83° C.

(19) 1-[N-(2-chloroethyl)-N-nitrosoureido]2-carboxyethylphosphonic acid diethyl ester: Yield: 72%; m.p.=90° C.

(20) 1-[N-(2-chloroethyl)-N-nitrosoureido]2-ethoxycarbonyl ethylphosphonic acid diethyl ester: Yield: 80%; m.p.=103° C.

The physical characteristics of the intermediates of the general formula IV are described in the following Table I

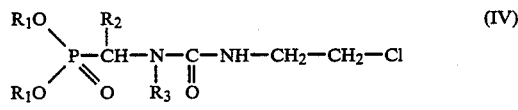

(IV)

TABLE I

| $R_1$ | $R_2$ | $R_3$ | Yld % | MP (°C.) | I.R. (cm$^{-1}$) $\nu$(NH) | I.R. (cm$^{-1}$) $\nu$(CO) | NMR |
|---|---|---|---|---|---|---|---|
| —$C_2H_5$ | —⟨phenyl⟩ | H | 80 | 82 | 3380 3250 | 1665 1550 | 1.05,t,3H: 1.35,t,3H; 3.50,m,4H; 3.80,q,2H; 4.30,q,2H; ($J_{PH}$ = 7Hz) 5.50,dd,1H ($J_{PH}$ = 23Hz; $J_{HH}$ = 10Hz) H exchangeable:6.50,m,1H; 7.50,m,1H; 7.50,m,5H Ar |
| —$C_2H_5$ | —$CH_3$ | H | 85 | <50 | 3200 3400 | 1650– 1690 1550 | 1.10 to 1.70,m,9H; 3.60,m,4H; 3.90 to 4.60,m,5H 2H exchangeable ~ 6.60 |
| —$C_2H_5$ | —⟨phenyl⟩—Cl | H | 70 | 122 | 3370 3290 | 1680 1550 | 1.00,t,3H; 1.50,t,3H; 3.50,m,4H; 3.70 to 4.60,m,4H; 5.50,d,1H; 6.45,s,1H exchangeable 6.40 to 7.70,m,5H of which 1H exchangeable. |

TABLE I-continued

| R₁ | R₂ | R₃ | Yld % | MP (°C.) | I.R. (cm⁻¹) ν(NH) | I.R. (cm⁻¹) ν(CO) | NMR |
|---|---|---|---|---|---|---|---|
| $-C_2H_5$ | ―⟨phenyl⟩―F | H | 95 | 105 | 3300, 3360 | 1685, 1550 | 1.00,t,3H; 1.50,t,3H; 3.50,m,4H; 3.60 to 4.50,m,4H 5.50,d,1H; 6.40,s,1H exchangeable 6.80 to 7.70,m,5H |
| $-C_2H_5$ | (CH₃)₂CH― | H | 96 | 115 | 3350 | 1680, 1550 | 0.90 to 1.60,m,12H; 1.70 to 2.50,m,1H; 3.60,m,4H; 3.80 to 4.60,m,5H; 6.60,m,2H exchangeable |
| $-C_2H_5$ | $CH_3-(CH_2)_2-$ | H | 88 | — | 3350 | 1680, 1550 | 0.70 to 1.70,m,13H; 3.50,m,4H; 3.80 to 4.30,m,5H 6.20 to 6.50,m,2H exchangeable |
| $-C_2H_5$ | $-CH_2-$⟨phenyl⟩$-OCH_3$ | H | 82 | — |  |  | 1.30,t,6H; 2.70 to 3.00,m,3H; 3.40,m,4H; 3.60,s,3H; 6.20,s,1H exchangeable; 6.50,d,1H exchangeable; 6.60 to 7.10; spectr. AB,4H |
| $-C_2H_5$ | $-CH_2-$⟨phenyl⟩ | H | 92 | 105 |  |  | 1.20,t,6H; 2.70 to 3.10,m,3H; 3.40,m,4H; 3.80 to 4.20,m,4H 6.20,s,1H exchangeable; 6.50,d,1H exchangeable; 7.10,s,5H Ar |
| $-C_2H_5$ | $-(CH_2)_3-$ | H | 95 | — | 3320 | 1640, 1535 | 1.30,t,6H; 1.70 to 2.30,m,4H; 3.20 to 3.60,m,6H 3.70 to 4.30,m,5H 6.50,s,1H exchangeable |
| $-C_2H_5$ | 2-Cl-C₆H₄-CH₂― | H | 86 | 97 |  |  |  |
| $-C_2H_5$ | 2-thienyl-CH₂― | H | 95 | 64 |  |  | 1.00 to 1.40,m,6H; 3.45,m,4H; 3.80 to 4.30,m,4H; 5.65,dd,1H; 6.40,s,1H exchangeable; 6.70 to 7.20,m,4H. |
| $-C_2H_5$ |  | H | 90 | — |  |  | C = 2 ethanol: Rotatory power $\alpha_D^{22} = +9.5°$ For other characteristics see 1st example of Table I |
| $-C_2H_5$ |  | H | 90 | — |  |  | C = 2 ethanol: Rotatory power $\alpha_D^{22} = -9.3°$ For other characteristics see 1st example of Table I |
| $-C_2H_5$ | H | $-CH_2-$⟨phenyl⟩ | 85 | 64 | 3310 | 1640, 1540 | 1.30,t,6H; 3.40 to 3.60,m,6H; 3.80 to 4.30,m,4H; 4.50,s,2H; 5.80,s,1H exchangeable; 7.20,s,5H |
| ―⟨phenyl⟩ | $-CH_3$ | H | 82 | 98 | 3340 | 1690, 1555 | 1.30,dd,3H ($J_{PH} = 17H_3$, $J_{HH} = 6.7$Hg 3.30,m,4H; 4.20 to 4.70,m,1H; 5.80,s,1H exchangeable; 6.15,d,1H exchangeable; 6.80 to 7.20,m,10H. |
| 2-OCH₃-C₆H₄― | $-CH_3$ | H | 86 |  |  |  | 1.30,dd,3H; 3.30,s,4H; 3.50,s,3H; 3.60,s,3H; 4.20 to 4.80,m,1H; 5.80 to 6.30,m,2H exchangeable. 6.50 to 7.10,m,8H. |
| $-C_2H_5$ | $-CH_2COOC_2H_5$ | H | 70 | 67 | 3380, 3440 | ester 1740, I. 1630, II. 1570 | 1.10 to 1.50,m,9H; 2.50 to 2.70,m,2H; 3.50,m,4H; 3.80 to 4.20,m,6H; 4.20 to 4.90,m,1H; 6.30 to 6.50,m,2H exchangeable. |
| $-C_2H_5$ | $-CH_2COOH$ | H | 55 | 144 | 3260, 3360 | 1720, 1630, 1570 | 1.20 to 1.40,t,6H; 2.30 to 2.70,m,2H 3.30 to 3.80,m,4H; 3.80 to 4.50,m,4H; 4.00 to 5.00,m,1H; Spectrum carried out in D₂O + DM₅₀. |

The physical characteristics of the general formula I are described in the following Table II $$\begin{array}{c} R_1O \\ \phantom{R_1O}\diagdown \\ \phantom{R_1O}P \\ R_1O\diagup\phantom{P}\diagdown \\ \phantom{xxxxxx}O \end{array} \begin{array}{c} R_2 \\ | \\ CH \end{array} - N - \begin{array}{c} R_3 \\ | \\ C \\ \| \\ O \end{array} - N - CH_2 - CH_2 - Cl \qquad (I)$$

with NO above the second N.

TABLE II

| EX | R₁ | R₂ | R₃ | I.R. (cm⁻¹) ν(NH) | I.R. (cm⁻¹) ν(CO) | NMR |
|---|---|---|---|---|---|---|
| 1 | —H | —CH₃ | H | | | 1.10 to 1.50,dd (J$_{PH}$ = 15.4Hz, J$_{HH}$ = 7Hz),3H; 3.50,t, (J = 6Hz),2H; 4.10,t,2H; 3.70 to 4.30,m,1H |
| 2 | —H | —C₆H₅ (phenyl) | H | | | 3.40,t,2H; 3.95,t,2H; 5.10,d, (J$_{PH}$ = 20Hz),1H; 7.20,m,5H. |
| 3 | —C₂H₅ | —C₆H₅ (phenyl) | H | 3180 | 1720 | 1.10,t,3H; 1.25,t,3H; 3.45,m,2H; 3.70 to 4.50,m, 6H; 5.55,dd, (J$_{PH}$ = 21Hz and J$_{HH}$ = 9Hz), 1H; 6.90 to 8.10,m,6H. |
| 4 | —C₂H₅ | —CH₃ | H | 3220 | 1720 | 1.20 to 1.80,9H; 3.40 to 3.70,m,2H; 3.90 to 5.00,m,5H; 7.40,m,1H exchangeable |
| 5 | —C₂H₅ | —C₆H₄—Cl (4-chlorophenyl) | H | 3180 | 1710 | 1.20,m,6H; 3.45,t,2H; 3.70 to 4.40,m,6H; 5.50,dd,1H; 7.40,s,4H; 7.80,m,1H exchangeable. |
| 6 | —C₂H₅ | —C₆H₄—F (4-fluorophenyl) | H | 3180 | 1715 | 1.00 to 1.50,m,6H; 3.30 to 4.40,m,8H; 5.50,m,1H; 6.90 to 8.00,m,5H. |
| 7 | —C₂H₅ | —CH(CH₃)₂ | H | 3220 | 1720 | 1.00 to 1.50,m,12H; 1.90 to 2.60,m,1H; 3.50,t,2H; 3.90 to 4.70,m,5H; 7.20,m,1H exchangeable. |
| 8 | —C₂H₅ | —(CH₂)₂—CH₃ | | 3220 | 1720 | 0.90 to 2.10,m,13H; 3.50,t,2H; 3.90 to 4.50,m,6H; 4.50 to 5.00,m,1H 7.30,m,1H exchangeable. |
| 9 | —C₂H₅ | —CH₂—C₆H₄—OCH₃ | H | 3230 | 1710 | 1.10,t,3H; 1.50,t,3H; 2.80 to 3.50,m,4H 3.90 to 4.50,m,6H; 3.75,s,3H; 4.50 to 5.00,m,1H; 6.70 to 7.30,m,4H; 7.40,m,1H exchangeable. |
| 10 | —C₂H₅ | —CH₂—C₆H₅ | H | 3240 | 1720 | 1.10,t,3H; 1.50,t,3H; 3.00 to 3.50,m,4H 3.90 to 4.50,m,6H; 4.50 to 5.00,m,1H; 7.30,s,5H; 7.60,m,1H exchangeable. |
| 11 | —C₂H₅ | —(CH₂)₃— | — | | 1690 | 1.10 to 1.50,m,6H; 1.80 to 2.70,m,4H; 3.40 to 4.00,m,4H; 4.00 to 4.50,m,6H; 4.80,m,1H. |
| 12 | —C₂H₅ | —CH₂—C₆H₄—Cl (2-chlorobenzyl) | H | 3240 | 1725 | 1.20 to 1.60,m,6H; 3.00 to 3.50,m,4H; 3.50 to 4.50,m,6H; 4.50 to 5.20,m,1H; 7.00 to 7.50,m,4H; 7.50,m,1H exchangeable. |
| 13 | —C₂H₅ | —(2-thienyl) | H | 3170 | 1720 | 1.00 to 1.50,2t,6H; 3.40 to 3.60,m,2H; 3.90 to 4.50,m,6H; 6.90 to 7.50,m,3H; 7.60 to 7.90,m,1H exchangeable. |
| 14 | —C₂H₅ | —C₆H₅ | H | Laevorotatory isomer | | α$_D^{22}$ = −34,4° (C = 2; CHCl₃) I.R. and NMR idem Example 2 |
| 15 | —C₂H₅ | —C₆H₅ | H | Dextrorotatory isomer | | α$_D^{22}$ = +36° C. (C = 2; CHCl₃) I.R. and NMR idem Example 3 |
| 16 | —C₂H₅ | —H | —CH₂—C₆H₅ | | 1690 | 1.20,t,3H; 1.40,t,3H; 3.30 to 4.50,m,10H; 4.90,s,2H; 7.40,s,5H. |
| 17 | —C₆H₅ | —CH₃ | H | 3220 | 1710 | 1.60,dd, (J$_{PH}$ = 17z, J$_{HH}$ = 7Hz),3H; 3.35,t,(J$_{HH}$ = 6Hz),2H; 4.400,t,(J = 6Hz),2H; 4.75,m,1H; 7.00,s,10H; 7.35,d,1H exchangeable |

TABLE II-continued

| EX | R₁ | R₂ | R₃ | I.R. (cm⁻¹) ν(NH) | I.R. (cm⁻¹) ν(CO) | NMR |
|----|----|----|----|----|----|-----|
| 18 | H₃CO—⟨phenyl⟩ | —CH₃ | H | 3380 | 1730 | 1.40 to 1.90,dd,3H; 3.30 to 3.60,t,2H; 3.80,2s,6H; 4.00 to 4.30,t,2H; 4.50 to 5.50, 5m,1H; 6.80 to 7.40,m,8H; 8.00,s,1H exchangeable. |
| 19 | —C₂H₅ | —CH₂COOC₂H₅ | H | 3240 | 1740 1720 1520 | 1.10 to 1.50,m,9H; 2.70 to 3.10,m,2H; 3.40 to 3.70,m,2H; 3.90 to 4.50,m,6H; 4.50 to 5.50,m,1H; 7.70 to 7.80,s,1H exchangeable. |
| 20 | —C₂H₅ | —CH₂COOH | H | 3280 | 1700 1710 1535 | 1.30 to 1.60,2t,6H; 2.80 to 3.30,m,2H; 3.40 to 3.60,m,2H; 4.00 to 4.60,m,4H; 4.50 to 5.50,m,1H. |

We claim:

1. Nitrosourea compound corresponding to the formula I $$\begin{array}{c} R_1O \\ \phantom{R_1O}\diagdown \\ \phantom{R_1O}\phantom{\diagdown}P \\ \phantom{R_1O}\diagup \\ R_1O \end{array} \begin{array}{c} R_2 \\ | \\ \!\!-\!\!CH\!\!-\! \\ \| \\ O \end{array} \begin{array}{c} R_3 \\ | \\ N\!\!-\! \\ \phantom{|} \end{array} \begin{array}{c} \\ C\!\!-\! \\ \| \\ O \end{array} \begin{array}{c} NO \\ | \\ N\!\!-\!CH_2\!\!-\!CH_2\!\!-\!Cl \\ \phantom{|} \end{array} \quad (I)$$

in which

R₁ represents hydrogen, alkyl having 1 to 6 carbon atoms or phenyl,

R₂ represents hydrogen, alkyl containing 1 to 6 carbon atoms, and which may carry a carboxy or alkoxycarbonyl radical including 2 to 6 carbon atoms; a thienyl, phenyl or benzyl radical which may carry a halogen atom or an alkyl or alkoxy radical containing 1 to 5 carbon atoms;

R₃ represents hydrogen, alkyl having 1 to 6 carbon atoms; or benzyl which may carry a halogen atom or an alkyl or alkoxy radical having 1 to 5 carbon atoms; or, alternatively, R₂ and R₃ together represent a group —(CH₂)ₘ— in which m has the value 3 or 4, in racemic form or in the form of optical isomers.

2. A compound of claim 1 which is α-[N-(2-chloroethyl)-N-nitrosoureido]benzyl-phosphonic acid diethyl ester.

3. A compound of claim 1 which is 1-[N-(2-chloroethyl)-N-nitrosoureido]ethyl-phosphonic acid diethyl ester.

4. A compound of claim 1 which is 1-[N-(2-chloroethyl)-N-nitrosoureido]ethyl-phosphonic acid diphenyl ester.

5. A compound of claim 1 which is 1-[N-(2-chloroethyl)-N-nitrosoureido]2-ethoxy-carbonylethylphosphonic acid diethyl ester.

6. Pharmaceutical composition for alleviating tumors susceptible thereto containing as active ingredient a compound according to any one of claims 1 to 5 in association or admixture with an excipient or an inert, pharmaceutically acceptable non-toxic carrier.

7. A method for treating a living animal body afflicted with a tumor responsive to such treatment, comprising the step of administering to the said living animal body having said tumor an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,567,169

DATED : January 28, 1986

INVENTOR(S) : Gilbert Lavielle and Claude Cudennec

It is certified that error appears in the above-identified patent and that said Letters Patent is hereby corrected as shown below:

Cols. 9 & 10, TABLE II, approximately line 55, last column, EX # 14 (line 8 from bottom of table) "Example 2" should read -- Example 3 --

Cols. 9 & 10, TABLE II, approximately line 66, last column, EX # 17 (line 2 from bottom of table) "4.400" should read -- 4.00 --

Cols. 11 & 12, TABLE II-continued, approximately line 6, last column, EX # 18, (line 8 from bottom of table) below the "t" delete the "1-" that interferes with that "t" and also underline the "t" like so -- $\underline{t}$ --

Signed and Sealed this

Twenty-seventh Day of May 1986

[SEAL]

Attest:

DONALD J. QUIGG

Attesting Officer

Commissioner of Patents and Trademarks